United States Patent [19]
Platica et al.

[11] Patent Number: 5,795,740
[45] Date of Patent: Aug. 18, 1998

[54] PITUITARY DIFFERENTIATION FACTOR AND METHODS OF USE THEREOF

[75] Inventors: Micsunica Platica; Ovidiu Platica, both of New York; James F. Holland, Scarsdale, all of N.Y.

[73] Assignee: Mount Sinai School of Medicine, New York, N.Y.

[21] Appl. No.: 890,572

[22] Filed: Jul. 9, 1997

Related U.S. Application Data

[60] Provisional application No. 60/021,589 Jul. 11, 1996.
[51] Int. Cl.$^6$ .................. C12N 15/00; C07K 14/435; C07H 21/04
[52] U.S. Cl. .................. 435/69.1; 536/23.5; 536/24.31; 435/172.3; 435/320.1; 435/325; 435/252.3; 530/530; 530/399; 935/8; 935/9; 935/22
[58] Field of Search .................. 536/23.5, 24.31; 435/172.3, 320.1, 325, 252.3, 69.1; 530/350, 399; 935/8, 9, 22

[56] References Cited

PUBLICATIONS

Platica et al. Endocrinology, 1992 131(6) 2573–2580.
Bani et al. (1994) Br. J. Cancer 70:900.
Mira–Y–Lopez et al. (1986) Proc. Nat., Acad. Sci USA 83: 7780.
Prats et al. (1989) Proc. Natl. Acad. Sci. USA 86:1836.
Tanigaki–Obana et al. (1994) Arch. Dermatol Res. 286:484.

Primary Examiner—Carla J. Myers
Attorney, Agent, or Firm—Baker & Botts

[57] ABSTRACT

The present invention is directed to pituitary differentiation factor (PDF), a pituitary factor that is capable of differentiating cells including breast cancer and prostatic cancer cells. Isolated nucleic acids encoding PDF and related vectors and host cells are also provided. Restoration of differentiating ability to malignantly transformed cells provides a modality of cancer therapy. The isolated and purified PDF of the invention is accordingly useful in the treatment of breast and prostatic cancer.

15 Claims, 7 Drawing Sheets

ACGCCAAGCTCTAATACGACTCACTATAGGGAAAGCTGGTACGCCTGCAGGTACCGGTCCGGAATTCC
CGGGTCGACGAATCCGCGGGNCGCCCTATAGTGAGTCGTATTACGCGCGATTNAGGTGACACTATAGN
CCGATTTAGGTGACACTATAGTCGATTTAGGTGACACTATAGTGAGTCGTATTAGAAGCTTGGCGATT
TAGGTGACACTATAGNCCGATTTAGGTGACACTATAGTCGATTTAGGTGACACTATAGTCGGGCCGCC
CTATAGTGAGTCGTATTAGGCGTCGATTTAGGTGACACTATAGTCGTATTAGCCGCCCTATAGTGAGT
CGTATTACGCGCCGATTTAGGTGACACTATAGTCGTATTAGCCGCCCTATAGTGAGTCGTATTACGCG
CCGATTTAGGTGACACTATAGNCGACGAATTCGCGGCCGCTCTAGAGGATCCAAGCTTACGTACGCGT
GCATGCGACGTCATNNTCTTCTTTAGTGTCAACCTAAATCAATCANTGGCCGCGGTTACAA

FIGURE 5

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 538 nucleic acids
        ( B ) TYPE: nucleic acid
        ( C ) STRANDEDNESS: single
        ( D ) TOPOLOGY: linear ( i i ) MOLECULE TYPE:

( i i i ) ORIGINAL SOURCE:
        ( A ) ORGANISM: human ( i v ) FEATURE:
        ( A ) NAME/KEY:
        ( B ) LOCATION:
        ( C ) OTHER INFORMATION: Pituitary Differentiation Factor ( v ) SEQUENCE DESCRIPTION: SEQ ID NO:1:

ACGCCAAGCT CTAATACGAC TCACTATAGG GAAAGCTGGT ACGCCTGCAG GTACCGGTCC    60

-continued

| | | | | | | |
|---|---|---|---|---|---|---|
| GGAATTCCCG | GGTCGACGAA | TCCGCGGNCG | CCCTATAGTG | AGTCGTATTA | CGCGCCGATT | 120 |
| NAGGTGACAC | TATAGNCCGA | TTTAGGTGAC | ACTATAGTCG | ATTTAGGTGA | CACTATAGTG | 180 |
| AGTCGTATTA | GAAGCTTGGC | GATTTAGGTG | ACACTATAGN | CCGATTTAGG | TGACACTATA | 240 |
| GTCGATTTAG | GTGACACTAT | AGTCGGGCCG | CCCTATAGTG | AGTCGTATTA | GGCGTCGATT | 300 |
| TAGGTGACAC | TATAGTCGTA | TTAGCCGCCC | TATAGTGAGT | CGTATTACGC | GCCGATTTAG | 360 |
| GTGACACTAT | AGTCGTATTA | GCCGCCCTAT | AGTGAGTCGT | ATTACGCGCC | GATTTAGGTG | 420 |
| ACACTATAGN | CGACGAATTC | GCGGCCGCTC | TAGAGGATCC | AAGCTTACGT | ACGCGTGCAT | 480 |
| GCGACGTCAT | NNTCTTCTTT | AGTGTCAACC | TAAATCAATC | ANTGGCCGCC | GGTTACAA | 538 |

PITUITARY DIFFERENTIATION FACTOR AND METHODS OF USE THEREOF

SPECIFICATION

This application bases its priority on Provisional Application No. 60/021,589, filed Jul. 11, 1996.

BACKGROUND OF THE INVENTION

Malignant transformation is characterized by uncoupling of proliferation and differentiation, leading to continuing amplification of cells with loss of their ability to progress to differentiation. Agents capable of restoring the differentiation ability of cancer cells are thus potentially useful in cancer therapy.

Various extracts, proteins and chemicals have been shown to induce differentiation of certain cancer cells in vitro and in vivo. For example, Sachs et al. (1987) *Cancer Research* 47: 1981 provide a review of induction of differentiation of leukemia myeloid hematopoietic cells, including observations that myeloid leukemia cells can be induced to differentiate in vitro and in vivo by a normal differentiating protein. Tallman et al. (1992) *J. Clin. Pharmacol.* 32: 868 review the role of retinoids in cancer treatment. Retinoids have been investigated as differentiating agents for the prevention and therapy of bladder and mammary cancers and leukemias. Platica et al. (1992) *Endocrinolog* 131: 2573 report that extracts of bovine pituitary and a rat mammosomatotropic tumor induce differentiation of rat mammary tumor cells.

Differentiation agents identified by in vitro studies and in vivo rodent studies have also been assessed clinically. For example, differentiation agents including hexamethylene bisacetamide and retinoic acid have entered clinical trials for cancer treatment and prevention and are reviewed by Linskey et al. (1995) *Neurosurgery* 36: 1. Successful use of differentiation agents for the treatment of acute promyelocytic leukemia has been reported by Warrell et al. (1993) *New Engl. J. Med.* 329: 177. Retinoids have been shown to be therapeutically useful in the treatment of cervical cancer by Lippman et al. (1993) *J. Natl. Cancer Inst.* 85: 499.

The clinical use of differentiation agents to induce cancer cells to differentiate and thus assume more normal characteristics has been termed differentiation therapy. Differentiation therapy provides an alternative approach to conventional cancer therapy such as cytotoxic chemotherapy. Accordingly, there is a need in the art for the identification and isolation or synthesis of new agents capable of promoting the differentiation of cancer cells.

SUMMARY OF THE INVENTION

The present invention is directed to pituitary differentiation factor (PDF), a pituitary factor that is capable of differentiating cells including breast cancer and prostate cancer cells.

In one embodiment, the present invention provides isolated nucleic acids encoding PDF. Vectors and host cells containing isolated nucleic acids encoding PDF are further provided.

Another embodiment of the present invention provides isolated and purified PDF and biologically active analogs and fragments thereof, and a method of making PDF and biologically active analogs and fragments thereof.

The present invention further provides a method of promoting differentiation of breast cancer or prostatic cancer cells comprising contacting the breast or prostatic cancer cells with a differentiation-promoting effective amount of PDF.

Another embodiment of the present invention provides a method of treatment of breast cancer or prostatic cancer comprising administering a therapeutically effective amount of PDF to a patient in need of such treatment.

In another embodiment of the present invention, pharmaceutical compositions are provided that include PDF or biologically active analogs or fragments thereof admixed with a pharmaceutically acceptable carrier.

BRIEF DESCRIPTION OF THE DRAWINGS

FIG. 5 provides the nucleotide sequence of SEQ ID NO:1.

DETAILED DESCRIPTION OF THE INVENTION

Figure 1:
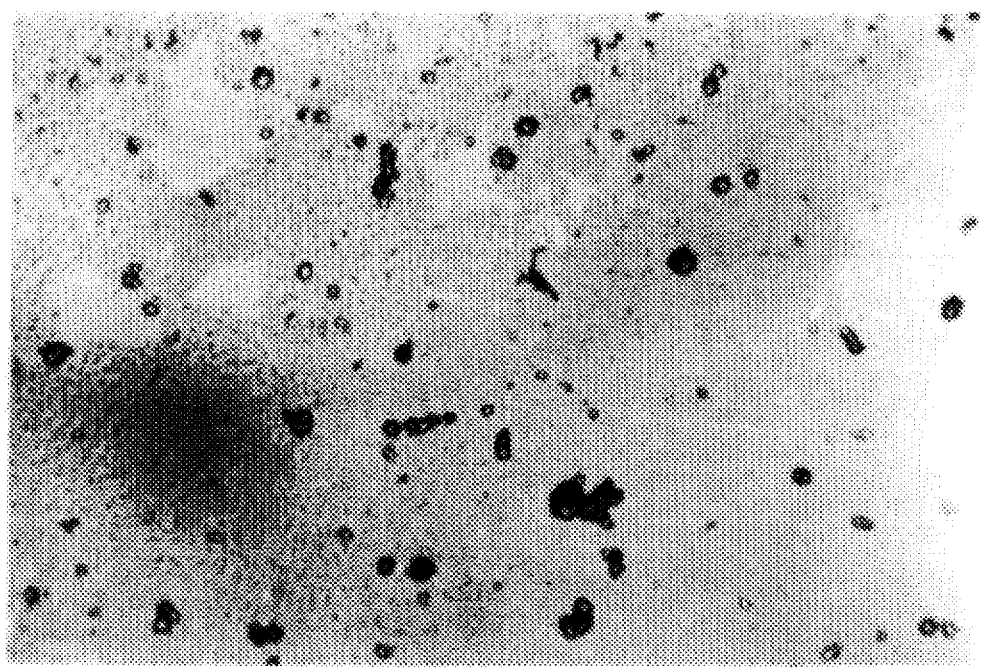
FIG. 1 depicts MCF-7 human breast cancer cells in conditioned medium in the absence of PDF.

The present invention is directed to pituitary differentiation factor (PDF). PDF is a polypeptide obtainable from mammalian pituitary and from pituitary tumors including MtTW10. PDF promotes the differentiation of cells including breast cancer and prostatic cancer cells.

In one embodiment the present invention provides an isolated nucleic acid encoding PDF. A plasmid designated pBS-PDF1 containing a 2.2 kB cDNA encoding PDF has been deposited on Jul. 8, 1996 with the American Type Culture Collection (ATCC), 12301 Parklawn Drive, Rockville, Md. 20852; in accordance with the Budapest Treaty and has been accorded accession number ATCC 97648. In a preferred embodiment, the isolated nucleic acid encoding PDF comprises the nucleotide sequence of SEQ ID NO: 1 set forth in FIG. 5.

In accordance with the present invention, an isolated nucleic acid encoding PDF may be obtained from mammalian pituitary by expression cloning. A mammalian pituitary cDNA library may be prepared by methods known to one of ordinary skill in the art, as described for example by Sambrook et al (1989) Molecular Cloning: *A Laboratory Manual*, 2nd edition, Cold Spring Harbor Laboratory Press, Cold Spring Harbor, N.Y. In addition, mammalian pituitary cDNA libraries are available commercially, for example from Clontech, Palo Alto, Calif. A human pituitary library is preferred.

An isolated nucleic acid encoding PDF was obtained from a mammalian cDNA library by expressing the cDNA clones of the library, and assessing the expressed product for PDF activity in a functional assay. Various expression systems are known to the ordinarily skilled artisan. In a preferred embodiment, Xenopus oocytes are used as the host for expression of the pituitary cDNA. The use of Xenopus oocytes for the expression of exogenous nucleic acids is known in the art and described, for example, by Gurdon et al. (1983) *Methods in Enzymology* 101: 370. Expression vectors containing pituitary cDNA under the control of a strong promoter can be injected into the nuclei of oocytes, after which oocytes are incubated for from one to several days, followed by assessment of oocyte lysates or conditioned media (CM) for PDF activity. Alternately, mRNA can be synthesized in vitro from pituitary cDNA, and injected into oocytes, followed by assessment of oocyte lysates or CM for PDF activity as described hereinbelow. The pituitary cDNA may be divided into pools from which RNA is synthesized, injected into oocytes, and tested for functional activity. Positive pools are divided into subpools and the protocol is repeated until a single cDNA encoding PDF is identified.

Bioassays useful for the identification of PDF are based upon the ability of PDF to promote the differentiation of breast and prostate cancer cells. Any breast or prostate cancer cells that are responsive to the differentiation-inducing activity of PDF as described herein are suitable for use in the bioassay of the present invention. Various cultured breast and prostate cancer cells are available from the ATCC. In a preferred nonlimiting embodiment, the breast cancer cells used for the bioassay are the rat mammary tumor cell line MTW9/P1 available from D. Sirbascu, University of Texas Medical School, Houston, Tex. or MCF-7 human breast cancer cells available from the ATCC. In another preferred embodiment, the prostate cancer cells are from the human prostate cell line DU145 available from the ATCC.

Treatment of breast or prostate cancer cells with PDF causes undifferentiated cancer cells to differentiate. Differentiation can be measured by morphological and biochemical parameters that are consistent with differentiation toward the structure of a normal mammary or prostate gland. The cancer cells, which normally grow in culture as single cell suspensions, aggregate and form spheroids within 24 hours of treatment with PDF. Aggregation may be measured by removing and counting suspended single cells, then detaching and counting the remaining aggregated and adherent cells, and then determining the percentage of total cells that have aggregated. A statistically significant increase in aggregation of treated cells as compared to untreated cells is evidence of PDF activity. The measurement of aggregation thus provides a simple and convenient bioassay for PDF activity.

The aggregation bioassay may be performed as follows. About $1 \times 10^5$ breast cancer cells, for example MTW9/P1 cells, are grown in 1 ml serum-free Dulbecco's modified Eagle's Medium (DMEM) in the presence or absence of the expression product of the pituitary cDNA at a concentration of from about 10 ng/ml to about 10 µg/ml. The cultures are incubated at 37° C. in a 5% $CO_2$ atmosphere for about 72 hours. Suspended single cells are removed by rinsing with serum-free DMEM and then counted. The remaining aggregated and adherent cells are detached by trypsinization with trypsin-EDTA for five minutes and then counted. Cells are conveniently counted by viewing cells by light microscopy on gridded culture dishes. A dose-responsive increase in aggregation in response to treatment with the pituitary cDNA expression product indicates that the cDNA encodes PDF.

A spheroid formation assay may be performed as follows. About $1 \times 10^5$ prostate cancer cells, for example DU145 cells, are grown in RPMI 1640 medium (Sigma) supplemented with 10% fetal bovine serum (FBS) (BioWhittacker, Walkersville, Md.), 10 IU penicillin/ml and 50 mg streptomycin/ml at 37° C. in a 5% $CO_2$ atmosphere. Cultures are treated with various concentrations of PDF, for example from 50–300 ug/ml culture. After 72 hours, cultures are scored for the formation of spheroids. Spheroids are defined as multicellular aggregates with no individual distinguishable cell morphology. Cultures are conveniently scored by viewing gridded culture dishes by light microscopy and counting spheroids. A dose-responsive increase in spheroid formation is indicative of PDF bioactivity.

In a modification of the foregoing aggregation bioassay, aggregation and spheroid formation may be detected by light microscopy or electron microscopy of fixed sections. After culturing and treating cells as described above, cultured cells are fixed and sectioned for microscopy by methods known in the art. For example, cultured cells are fixed in 1.5% glutaraldehyde in 0.1 M cacodylate buffer for one hour. Pellets obtained by low speed centrifugation are postfixed in 1.5% osmium tetroxide in collidine buffer for 30 minutes, followed by 30 minutes in uranyl acetate in maleate buffer, and then dehydrated and embedded in Epon 812. For light microscopy, 1 µm sections are stained with methylene blue, azure-II, and basic fuchsin. For electron microscopy, 60 to 90 nm sections are cut and stained with uranyl acetate-lead citrate. Aggregation and spheroid formation can then be visualized by light or electron microscopy. A statistically significant increase in aggregation and spheroid formation of treated cells as compared to untreated cells is evidence of PDF bioactivity.

Treatment of breast cancer cells with PDF produces other effects that can be observed by microscopy, thus providing further PDF assays. By light microscopy, it can be observed that PDF-treated cells are smaller in size than untreated cells, and are clustered in organoid structures consistent with gland formation. By electron microscopy it can be observed that treated cells are smaller, with smaller nuclei than untreated cells. Further, the cytoplasm is rich in polarized organelles such as lysosomes and endoplasmic reticulum, as opposed to untreated cells that have vacuolated cytoplasm, with few organelles other than mitochondria.

Breast cancer cells treated with PDF also undergo biochemical changes that provide additional bioassays for PDF. Specifically, lactalbumin, which is secreted only in differentiated mammary cells, is produced by PDF-treated MTW9/P1 cells but not by untreated cells. Thus the synthesis of lactalbumin, as detected, for example, by conventional Northern or Western blotting, histochemical techniques, or immunoassays provides another bioassay for PDF.

By the foregoing cloning methods and bioassays, an isolated cDNA encoding PDF has been identified. It has thus been discovered in accordance with the present invention that a single nucleic acid encoding a single polypeptide directs the pituitary differentiating activity.

The isolated nucleic acid encoding PDF may be additionally characterized by its nucleotide sequence. Nucleotide sequencing may be accomplished by methods known to one of ordinary skill in the art, including for example the dideoxy chain termination method of Sanger et al. (1977) *Proc. Natl. Acad. Sci.* 74: 5463. An isolated nucleic acid encoding PDF in accordance with the present invention contains the sequence set forth at SEQ ID NO:1 in FIG. 5.

The present invention encompasses isolated nucleic acids that can be obtained from mammalian pituitary and pituitary tumors and that encode PDF, a polypeptide having the ability to promote the differentiation of breast cancer cells as determined by any of the above-described bioassays. In a preferred embodiment, the nucleic acid is the 2.2 kB nucleic acid contained in plasmid pBS-PDF1 and comprising the sequence set forth at SEQ. ID NO:1 in FIG. 5. In another preferred embodiment, the isolated nucleic acid is a contiguous fragment of the 2.2 kB insert wherein the fragment encodes biologically active PDF. The ordinarily skilled artisan can obtain fragments of the 2.2 kB insert by conventional molecular biological techniques, prepare expression vectors containing the fragments, express the nucleic acid, and assay the resulting product for PDF activity as described hereinabove to identify fragments that encode PDF.

Isolated nucleic acids encoding PDF can also be obtained by using synthetic nucleic acids having the sequence of SEQ ID NO:1 or fragments thereof as probes to isolate the desired nucleic acid from a pool of pituitary nucleic acids. Suitable methods are described, for example, by Sambrook et al.

In a preferred embodiment of the present invention, the isolated nucleic acid encoding PDF is contained in the 2.2 kB insert of plasmid pBS-PDF1. The present invention further encompasses analogs of the nucleic acid contained in the 2.2 kB insert of plasmid pBS-PDF1 wherein said analogs encode PDF. For example, the ordinarily skilled artisan, with the knowledge of the degeneracy of the genetic code, can determine nucleic acid sequences that encode the amino acid sequence encoded by the insert of plasmid pBS-PDF1. Further, the sequence can be selected to optimize expression in a particular host organism by utilizing known preferred codons for a host organism of choice. In addition, analogs may be made by making substitutions or deletions of residues that are not necessary for biological activity. Such analogs may be identified by the bioassays described above.

The present invention further encompasses nucleic acids isolatable from mammalian pituitary or pituitary tumors and capable of hybridizing under moderate or high stringency conditions to the 2.2 kB insert of plasmid pBS-PDF1 or to an isolated nucleic acid having the sequence of SEQ ID NO:1 or its complement and further capable of encoding biologically active PDF. Moderate and high stringency hybridization conditions are known to the skilled artisan and described, for example, in Sambrook et al. and Beltz et al. (1983) Methods Enzymol. 100: 226. High stringency conditions include, for example, hybridization at 68° C. in aqueous buffered solution or at 42° C. in 50% formamide. Moderate stringency conditions are typically achieved by reducing the temperature, reducing the amount of formamide, or increasing the ionic strength of the aqueous solution. The ability of the isolated nucleic acid of the present invention to encode biologically active PDF can be determined by the functional assays described hereinabove.

The present invention is further directed to vectors comprising the isolated nucleic acids of the present invention. The vectors are useful for the amplification and/or expression of the nucleic acids encoding PDF. In one embodiment, the vectors of the present invention comprise the nucleic acid encoding PDF operably linked to suitable transcriptional and/or translational regulatory elements to effect expression of PDF in a suitable host cell. The regulatory elements may be derived from mammalian, microbial, viral or insect genes, and include, for example, promoters, enhancers, transcription and translation initiation sequences, termination sequences, origins of replication, and sequences encoding leader and transport sequences. Suitable regulatory elements are selected for optimal expression in a desired host cell. Useful expression vectors can be constructed by methods known to one of ordinary skill in the art, and are also commercially available. Recombinant viral vectors, including retrovirus, parvovirus, densovirus and baculovirus vectors are particularly preferred.

In a preferred embodiment, the expression vector comprises a strong constitutive or inducible promoter operatively linked to a nucleic acid encoding PDF. Suitable promoters are well known and readily available to one of ordinary skill in the art and include, for example, bacterial, yeast, viral, mammalian, and insect promoters. Expression vectors compatible with insect and mammalian cells are particularly preferred.

Another embodiment of the present invention provides host cells comprising a nucleic acid encoding PDF. Host cells comprising the nucleic acid are useful for replicating and expressing the nucleic acid encoding PDF. The host cell may be procaryotic or eucaryotic, including bacterial, yeast, insect or mammalian cells. Insect and mammalian cells are preferred. Particularly preferred host cells are insect cell lines including, for example, Spodoptera frugiperda and Trichoplusia ni cells.

The isolated nucleic acids or expression vectors may be introduced into the host cells by methods known to one of ordinary skill in the art, including transformation, transfection and infection. For example, transfection may be accomplished by known methods such as liposome mediated transfection, calcium phosphate mediated transfection, naked DNA transfection, microinjection and electroporation. Transformation methods of procaryotic cells are described, for example, by Cohen et al. (1972) Proc. Natl. Acad. Sci. USA 69: 2110. Transformation of eucaryotic host cells is described, for example, by Sambrook et al.

Expression systems utilizing baculovirus vectors and insect host cells are also preferred. The use of baculoviruses as recombinant expression vectors to infect lepidopteran insect cells is known in the art and described for example by Luckow et al. (1988) BioTechnology 6: 47.

The present invention is further directed to isolated and purified PDF and biologically active analogs and fragments thereof. In a preferred embodiment of the present invention, the isolated and purified PDF has an amino acid sequence encoded by the DNA in plasmid pBS-PDF1.

Isolated and purified PDF may be made by introducing a nucleic acid encoding PDF into a suitable host cell, for example by transformation, transfection or injection, culturing the host cell under conditions suitable for expression, and recovering recombinant PDF. Recombinant PDF may be recovered from cells or culture medium by protein purification methods known in the art. In a preferred embodiment, an expression vector comprising a nucleic acid encoding PDF under the control of a suitable promoter is introduced into an insect or mammalian host cell.

Biologically active analogs and fragments of PDF are similarly made utilizing a nucleic acid encoding a biologically active analog or fragment of PDF. The isolated recombinant analog or fragment may be identified by the bioassay described above. The term "analogs" includes substitutions and alterations of the amino acid sequence of PDF, which substitutions and alterations maintain the biological activity of PDF. Amino acid insertional derivatives include amino and carboxy terminal fusions and single or multiple intrasequence insertions. Deletional variants have one or more amino acids removed from the sequence. In substitutional amino acid variants, at least one residue has been removed or replaced by a different residue. Biologically active fragments are fragments of PDF or PDF analogs that do not encompass the entire length of the PDF polypeptide but which maintain the biological activity of PDF. The biologically active analogs and fragments may be made by recombinant methods as described for example by Sambrook et al, or by peptide synthetic techniques well known in the art such as solid phase peptide synthesis.

The present invention provides a method of promoting differentiation of breast cancer or prostatic cancer cells comprising contacting the breast or prostatic cancer cells with a differentiation-promoting effective amount of PDF or an analog or fragment thereof. A differentiation promoting effective amount of PDF is that amount that promotes differentiation of cancer cells by any of the above-described bioassays for differentiation.

Another embodiment of the present invention provides a method of treatment of breast cancer comprising administering a therapeutically effective amount of PDF or an analog or fragment thereof to a patient in need of such treatment. A therapeutically effective amount of PDF for breast cancer treatment is an amount that leads to change in the behavior of sentinel tumor masses such as morphologic or biochemical differentiation, reduction in tumor markers, tumor regression, apoptosis, or partial cessation of tumor growth or invasion. PDF is administered as a pharmaceutical composition containing PDF or a biologically active analog or fragment thereof and a pharmaceutically acceptable carrier.

Another embodiment of the present invention provides a method of treatment of prostate cancer comprising administering a therapeutically effective amount of PDF or an analog or fragment thereof to a patient in need of such treatment. A therapeutically effective amount of PDF for prostate cancer treatment is an amount that results in change in behavior of sentinel tumor masses as described hereinabove. PDF is administered as a pharmaceutical composition containing PDF or a biologically active analog or fragment thereof and a pharmaceutically acceptable carrier.

The formulation of pharmaceutical compositions is generally known in the art and reference can conveniently be made to Remington's Pharmaceutical Sciences, 17th ed., Mack Publishing Co., Easton, Pa. Formulation of PDF and biologically active analogs and fragments thereof for use in present invention must be stable under the conditions of manufacture and storage and must also be preserved against the contaminating action of microorganisms such as bacteria and fungi. Prevention against microorganism contamination can be achieved through the addition of various antibacterial and antifungal agents.

The pharmaceutical forms of PDF suitable for administration include sterile aqueous solutions or dispersions and sterile powders for the extemporaneous preparation of sterile injectable solutions or dispersions. In all cases, the form must be sterile and must be fluid to the extent that easy syringability exists. Typical carriers include a solvent or dispersion medium containing, for example, water buffered aqueous solutions (i.e., biocompatible buffers), ethanol, polyols such as glycerol, propylene glycol, polyethylene glycol, suitable mixtures thereof, surfactants, or vegetable oils.

Sterilization can be accomplished by an art-recognized technique, including but not limited to filtration or addition of antibacterial or antifungal agents, for example, paraben, chlorobutanol, phenol, sorbic acid or thimerosal. Further, isotonic agents such as sugars or sodium chloride may be incorporated in the subject compositions.

Production of sterile injectable solutions containing the subject PDF is accomplished by incorporating these compounds in the required amount in the appropriate solvent with various ingredients enumerated above, as required, followed by sterilization, preferably filter sterilization. To obtain a sterile powder, the above solutions are vacuum-dried or freeze-dried as necessary.

The subject PDF or analogs and fragments thereof are thus compounded for convenient and effective administration in pharmaceutically effective amounts with a suitable pharmaceutically acceptable carrier and/or diluent in a therapeutically effective dose.

As used herein, the term "pharmaceutically acceptable carrier and/or diluent" includes any and all solvents, dispersion media, antibacterial and antifungal agents, microcapsules, liposomes, cationic lipid carriers, isotonic and absorption delaying agents and the like which are not incompatible with the active ingredients. The use of such media and agents for pharmaceutical active substances is well known in the art. Supplementary active ingredients may also be incorporated into the compositions and used in the methods of present invention.

The precise therapeutically effective amount of PDF, analog or fragment thereof to be used in the methods of this invention applied to humans can be determined by the ordinary skilled artisan with consideration of individual differences in age, weight, extent of disease and condition of the patient. It can generally be stated that the PDF pharmaceutical preparation of the present invention should be preferably administered in an amount of at least about 1 mg per infusion dose, and more preferably in an amount up to about 10 mg per dose, or at a dose that achieves a local breast or prostate tissue concentration of from about $10^{-9}$M to $10^{-6}$M.

It is especially advantageous to formulate parenteral compositions in dosage unit form for ease of administration and uniformity of dosage. Dosage unit form as used herein refers to physically discrete units suited as unitary dosages for the mammalian subjects to be treated, each unit containing a predetermined quantity of active material calculated to produce the desired therapeutic effect in association with the required pharmaceutical carrier. The specification for the novel dosage unit forms of the invention are dictated by and directly depend on the unique characteristics of the active material (i.e., PDF, analogs, or fragments thereof), and the limitations inherent in the art of compounding such an active material for the treatment of breast or prostatic cell cancer.

The principal active ingredient is compounded for convenient and effective administration in effective amounts with a suitable pharmaceutically acceptable carrier in dosage unit form as hereinabove disclosed. In the case of compositions containing supplementary active ingredients, the dosages are determined by reference to the usual dose and manner of administration of the ingredients.

In the method of treatment according to the present invention, the PDF, analogs or fragments thereof may be administered in a manner compatible with the dosage formulation, in such amount as will be therapeutically effective, and in any way which is medically acceptable for the treatment of breast or prostatic cell cancer. Possible administration routes include injections by parenteral routes such as intravascular, intravenous, intraarterial, subcutaneous, intramuscular, intratumor, intraperitoneal, intraventricular or intraepidural. The compositions may also be directly applied to tissue surfaces, for example, during surgery. Sustained release administration is also specifically included in the invention, by such means as depot injections or erodible implants.

The invention is further illustrated by the following specific examples which are not intended in any way to limit the scope of the invention.

EXAMPLE 1

Pituitary Extracts Induce Differentiation Of Breast Cancer Cells and Prostatic Cancer Cells Extracts prepared from bovine pituitary and from a mammosomatotropic pituitary tumor were assessed for ability to induce differentiation of breast cancer cells.

Alkaline pituitary extracts of the mammosomatotropic tumor MtTW10 and the pituitary tumor MTW9-0M obtained from Dr. Untae Kim, Roswell Park Memorial Institute, Buffalo, N.Y. were prepared as described by Platica et al. (1992) *Endocrinology* 1: 2573. Bovine pituitary extract was obtained commercially from Collaborative Research, Bedford, Mass.

Pituitary extracts were added to serum-free cultures of MTW9/P1 rat mammary tumor cells, MCF-7 human breast cancer cells, normal epithelial breast cells, and myelocytic and lymphocytic leukemic cells. After twenty-four hours, breast cancer cells, which normally grew as single cell suspensions, aggregated and formed spheroids. Electron microscopy demonstrated changes indicating differentiation toward the structure of a normal mammary gland including polarization of organelles, lumen-like formation, junction formation, and appearance of intracellular secretory granules. Northern and Western blots performed by standard methods demonstrated that pituitary extract induced expression of laminin, casein and lactalbumin, and overexpression of E-cadherin, in breast cancer cells. Normal epithelial cells and myelocytic and lymphocytic leukemic cells were unaffected by treatment with pituitary extract.

Prostatic cancer cells were obtained from the ATCC. Serum-free cultures of the prostatic cancer cells were treated with pituitary extract prepared by Platica et al. as described above and assessed morphologically and biochemically for evidence of differentiation. Pituitary extract induced differentiation of prostatic cancer cells as measured by bioassay.

Extracts were similarly prepared from rat liver and kidney and added to cell cultures as described above. Rat liver and kidney extracts had no effect on differentiation of breast cancer or prostatic cancer cells.

Various hormones and growth factors, including epidermal growth factor (EGF), transforming growth factor (TGF), platelet-derived growth factor (PDGF), fibroblast growth factor (FGF), insulin-like growth factor (IGF) -I and -II, estradiol, growth hormone and prolactin, were added to cultures of breast cancer cells and assessed for differentiation activity as described above. None of the hormones or growth factors exhibited the ability to induce differentiation.

EXAMPLE 2

Identification of a Cloning System for Pituitary Differentiating Activity

An expression cloning method was devised to further characterize the pituitary differentiation activity. To determine whether Xenopus oocytes were an appropriate expression system, Xenopus oocytes were assessed for absence of pituitary differentiation-like activity, toxicity for breast cancer cells in the selected functional assay, and presence of factors that may destroy or interfere with pituitary differentiation activity.

The aggregation bioassay for pituitary differentiation activity measured spheroid formation of MCF-7 breast cancer cells. MCF-7 cells aggregate and form spheroids in response to the pituitary differentiation-activity of pituitary extract. Spheroids were visualized by light microscopy.

Oocyte lysate was obtained by homogenization of oocytes in 0.15M NaCl, followed by centrifugation for 30 minutes at 15.000 xg at 4° C. and collection of supernatant. Various amounts of oocyte lysate containing 50–400 µg of protein and conditioned medium in which oocytes were kept for 24 hours, were added to 1 ml. cultures containing $1\times10^5$ MCF-7 cells, followed by incubation at 37° C. for 72 hours. No morphological changes or toxic effects on MCF-7 cells were observed at any concentration of lysate or medium, indicating that Xenopus oocytes do not contain a pituitary differentiation-like activity, and that oocyte lysate is not toxic to breast cancer cells.

To determine whether the pituitary differentiation activity remains active in the presence of Xenopus oocyte lysate, cultures containing $1\times10^5$ MCF-7 cells were incubated with 150 µg/ml pituitary extract at 37° C. for 72 hours in the presence or absence of varying amounts of oocyte lysate (50–400 µg/ml). The aggregation effect induced by pituitary extract was unaffected by the presence of oocyte lysate. These results indicated that the pituitary differentiation activity remains active in the presence of Xenopus oocyte lysate.

Figure 6:
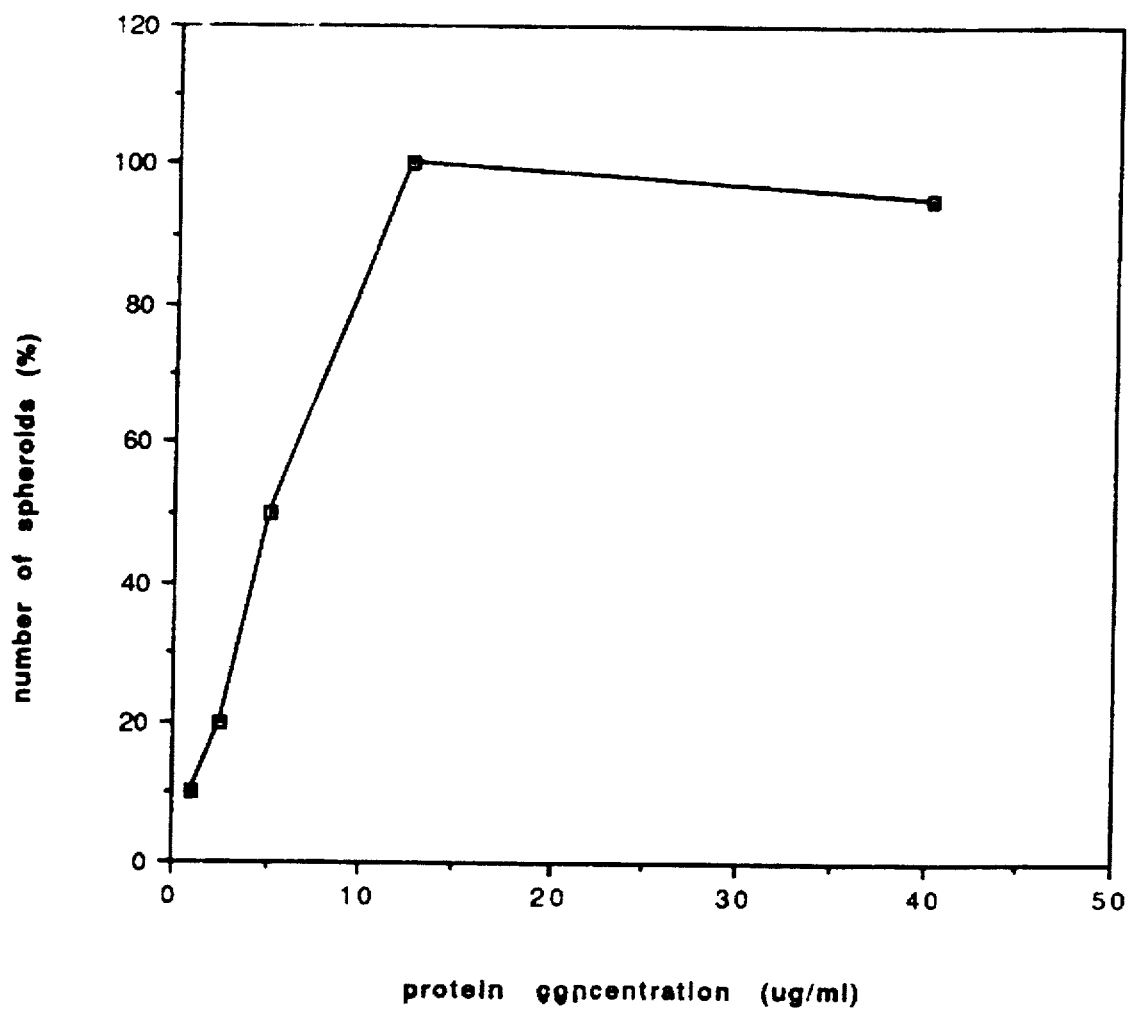
FIG. 6 is a graph demonstrating the effect of oocyte lysate containing PDF on spheroid formation in MCF-7 cells.

The ability of Xenopus oocytes to express the pituitary differentiating activity in amounts sufficient for detection by the aggregation bioassay was determined. Poly $(A)^+$ RNA from the rat pituitary tumor MtTW10 was prepared by the guanidinium/cesium chloride (CsCl) centrifugation method as described by Sambrook et al. in an RNAse free environment. Briefly, one gram of tissue was homogenized in 5 ml of 4M guanidinium thiocyanate, 0.1 Tris-HCl (pH 7.5) and 1% 2-ME, at room temperature. Then 9.7 ml homogenate was layered on a 3.3 ml pad of 5.7M CsCl and 4 mM EDTA Ph 7.5 and centrifuged at 30,000 rpm for 24 hours at room temperature. The RNA, pelleted at the bottom of the tube, was dissolved in 10 mM Tris pH 7.4, 1 mM EDTA, 0.1% SDS and then ethanol precipitated. The poly(A)+RNA was obtained by twice passing the total RNA on an oligo dT cellulose column. Seventeen micrograms of poly$(A)^+$RNA were obtained from 900 µg total RNA. Then, 20 fully grown oocytes (stage V and VI), kept in sterile MBS solution at 19° C., were injected with 5 ml containing 50 ng mRNA per oocyte, using an automatic syringe. The oocytes were then placed in MBS solution containing penicillin and streptomycin and incubated at 19° C. After 3 days the supernatants from oocyte lysates (prepared as described above) and conditioned medium (CM) from RNA-injected oocytes were tested for pituitary differentiating activity. Cultures containing $1\times10^5$ MCF-7 cells in 1 ml serum free RPMI were incubated in the presence of various protein concentrations of oocyte lysate (10–300 µg) or CM (50–200 µl/culture), at 37° C. in a 5% $CO_2$ atmosphere. After 72 hours, aggregation was seen in MCF-7 cultures treated with the oocyte lysate, but not in CM-treated MCF-7 cells. A linear relationship between the number of aggregates obtained and the lysate protein concentration was seen, as shown in FIG. 6.

Similar experiments were performed using rat liver poly $(A)^+$RNA. Neither the conditioned medium, nor the lysates from oocytes injected with liver mRNA had any effect on MCF-7 cells.

These results indicated that pituitary differentiation activity can be detected by the aggregation bioassay even when the whole population of pituitary MRNA was expressed in Xenolus oocytes.

The foregoing results demonstrate that Xenopus occytes do not contain a pituitary differentiating-like activity, are not toxic for MCF-7 cells, and do not destroy the pituitary differentiating activity. Further, Xenopus oocytes injected with pituitary MRNA expressed pituitary differentiating activity at a level detectable by the aggregation bioassay.

EXAMPLE 3

Characterization of Pituitary Differentiating Activity

A human pituitary cDNA library was obtained from Clontech, Palo Alto, Calif. and tested for the presence of cDNA encoding pituitary differentiating activity. The cDNA library was directionally cloned in the EcoRI-HindIII site of lambda Bluemid phage, which allows the transcription of either strand of DNA inserts with T7 or T3 RNA polymerases. Five µl of serial dilutions of phage library were mixed with 200 µl K802 E. coli ($OD_{600}$=0.25) and incubated at 37° C. for 20 minutes. Then, 3 ml of 0.7% agar molten at 48° C. were added and the mixture was spread on top of a 100 mm plate containing 1.5% LB agar. After incubation at 37° C. overnight the plaques were counted for each phage dilution and the library titer determined to be $1\times10^{10}$ pfu/ml. Then a pool of 400,000 pfu from the library was plated on 20 plates (20,000 pfu per plate) and incubated at 37° C. until the plaques reached about 1 mm in diameter. The top agar was then harvested in SM buffer (0.1M NaCl, 10 mM $MgSO_4.7H_2O$, 10 mM Tris-HCl, pH 7.5, 2% gelatin) and the bacterial cells lysed with chloroform. The agar and bacterial debris were pelleted by centrifugation at 8,000 xg for 20 minutes. The supernatant was treated with 1 µg/ml DNase I and 5 µg/ml RNase A for 1 hour at 37° C. and then recentrifuged at 8,000 rpm for 20 minutes. The supernatant, containing the phage particles, was centrifuged at 25,000 rpm (Beckman, SW27 ROTOR) for 2 hours at 20° C. The pelleted phages were then resuspended in 0.5M Tris buffer pH 8, incubated with 100 µg/ml proteinase K for 30 minutes at 37° C., followed by three phenol, one phenol/chloroform and one chloroform extraction and ethanol precipitation.

Since in this library the T3 RNA polymerase synthesizes the (+) strand of cloned inserts, the phage DNA was linearized by digestion with Sal I which cuts in the polycloning region on the site of the insert opposite to T3 RNA polymerase promoter. For efficient translation, a CAP site was added to the 5' end of transcripts. The transcription followed Melton's protocol (Krieg et al., 1987, Methods Enzymol. 155 397) with minor modifications as described by Regec et al. (1995) Blood 85: 2711 using a mMessage mMachine kit from Ambion which can generate 30–50 µg of capped RNA 10 per each µg of plasmid DNA. The reaction was carried out in 20 µl volume using 5 µg linearized phage DNA and the protocol and reagents provided by manufacturer. After a one hour incubation at 37° C., 1U RNase free DNase I was added for each µg of DNA and the incubation continued for 15 minutes. Then the reaction mixture was phenol/chloroform extracted, followed by precipitation with half volume 7.5 $MNH_4$ acetate and three volumes of ethanol. With three such successive ethanol precipitations, 99% of unincorporated nucleotides were removed.

Twenty oocytes were injected with 50 ng RNA per oocyte, as described above, placed in MBS solution containing penicillin and streptomycin, and incubated at 19° C. for 3 days. The oocyte lysate, prepared as described above, was then tested for differentiating activity on MCF-7 cells using the above-described bioassay. The treated cells formed spheroids, similar to those formed by these human breast cancer cells in the presence of pituitary extract. A linear relationship between the number of spheroids formed and the protein lysate used in the bioassay was seen. (Please provide data). These data show that the Clontech human pituitary cDNA library contains one or more clones encoding for pituitary differentiating activity.

The above-described pool of 400,000 pfu from the pituitary cDNA library was used for sib selection. From the 400,000 pfu pool, ten subpools of about 40,000 plaques each were plated separately and grown until they reached about 1 mm in size. The phage DNA from each pool was prepared, and capped transcripts were synthesized with T3 RNA polymerase as described. RNA from each subpool was injected into 20 frog oocytes (50 ng/oocyte) and the lysates were tested for differentiating activity on MCF-7 cells. For each bioassay, controls with mRNA from pituitary tumors, with lysate from non-injected oocytes and with pituitary extracts were prepared. Of the ten subpools analyzed, three showed aggregating activity in the bioassay. Subpool #2 displayed the strongest biological activity and was selected for further sib selection. This subpool was divided in 10 subpools of about 4,000 pfu each, which were processed as above. From these subpools, the subpool #6 was shown to have the strongest differentiating activity, and was further divided in ten subpools (each containing above 400 pfu) which were processed similarly. Subpool #4 was found to contain the highest differentiating specific activity, and was used for further sib selection. This process was continued by further dividing positive pools and screening for differentiation activity until a single positive clone encoding pituitary differentiating factor (PDF) was identified. The identified PDF cDNA phage clone was converted into a plasmid clone following the procedure of clontech. The phage DNA was digested with NotI to release the pBLUESCRIPT plasmid DNA containing the cDNA insert. After phenol chloroform extraction and ethanol precipitation, the digested plasmid DNA was ligated and used to transform competent DM5 alpha E. coli (Gibco, BRL). The colonies were grown on agar plates with 50 µg/ml ampicillin, and contained the Bluescript plasmid with the cloned PDF cDNA.

Figure 2:
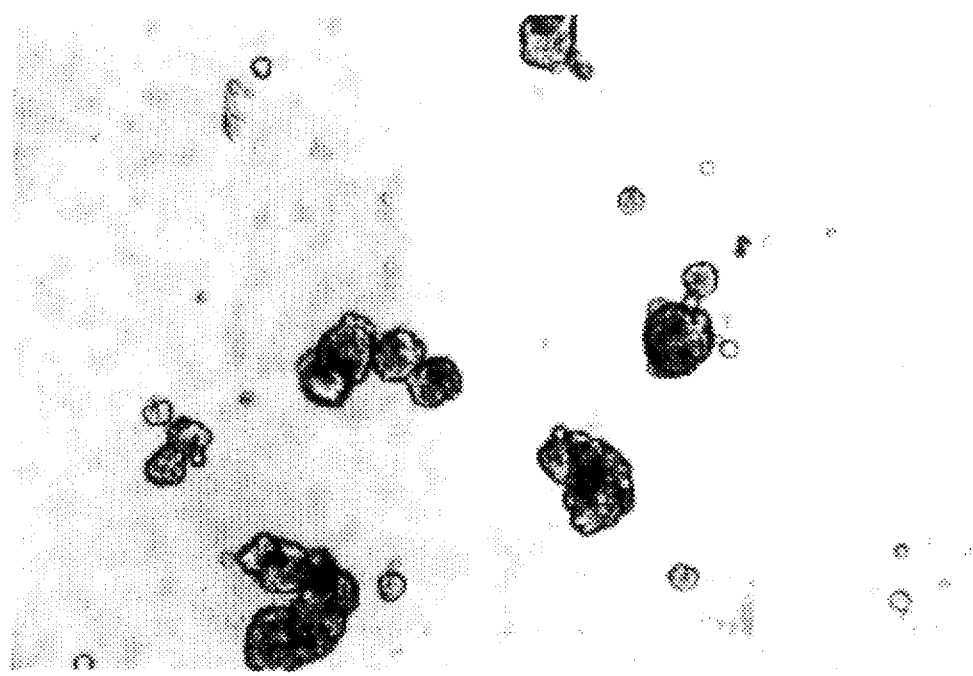
FIG. 2 depicts MCF-7 human breast cancer cells treated with lysate of oocytes injected with cDNA encoding PDF, and illustrates aggregation induced by PDF.

To ensure that the plasmid clone contained cDNA encoding PDF, the transcript from the cDNA was synthesized with T3 RNA polymerase and translated in Xenopus oocytes. The oocyte lysate was tested for PDF activity as described above. FIG. 1 depicts MCF-7 cells incubated with control CM. FIG. 2 depicts MCF-7 cells treated with lysate of oocytes containing the cDNA transcript. The treated cells aggregated and formed spheroids, thus confirming that the cDNA clone encoded PDF. The plasmid DNA was then prepared for sequencing.

Five hundred ml ampicillin/LB media inoculated with 0.5 ml stock suspension of E. coli carrying the plasmid containing the PDF cDNA was incubated, with shaking, at 37° C. overnight. The next day the cells were pelleted at 8,000 xg for 20 minutes at 4° C. and plasmid DNA prepared by alkaline lysis method of Birnboim and Dolly (1979) Nucleic Acid Res, 7: 1573. The bacterial pellet was resuspended in 10 ml 50 mM glucose, 25 mM Tris-HCl (pH 8.0) and 10 mM EDTA (pH 8.0). After treatment with lysozyme, the bacterial cells were lysed with 0.2N NaOH, 1% SDS, for 10 minutes at room temperature. Then, 15 ml of 3M cold potassium acetate was added. The mixture was stored on ice for ten minutes and centrifuged at 4000 xg for 15 minutes at 4° C. The supernatant containing primarily plasmid DNA was filtered and precipitated with 0.6 volumes of isopropanol. The nucleic acid was sedimented by centrifugation at 5,000 rpm for 15 minutes, washed with 70% ethanol and dissolved in TE buffer.

CsCl/ethidium bromide gradients were prepared according to Sambrook et al. (1989) Molecular Cloning: A Laboratory Manual, 2nd edition, Cold Spring Harbor Laboratory Press, Cold Spring Harbor, N.Y. One gram of CsCl was dissolved in each ml of plasmid preparation and 80 ul of ethidium bromide (10 mg/ml) were added to each ml of CsCl DNA solution. After the centrifugation at 60,000 rpm for 24 hours at 20° C. in a Ti 65 rotor, the bacterial DNA was separated in two bands: the upper band containing the linear, chromosomal and nicked circular plasmid DNA and the lower band consisting of closed circular supercoiled plasmid DNA. The plasmid DNA was recovered, ethidium bromide extracted with 1-butanol and after removing CsCl by dialysis, the DNA was precipitated with ethanol.

The PDF cDNA sequencing was performed in the Core Facility of Mount Sinai Medical School, New York, using the dideoxy chain termination method of Sanger et al. (1977) Proc. Natl. Acad. Sci. 74: 5463. Each portion of the clone was sequenced from both forward and reverse orientations. 530 nucleotides of the 2.2 kB insert were sequenced using M13-20 and reverse primers from Bluescript plasmid sequence. The 530 base pairs of the PDF cDNA have the nucleotide sequence set forth in SEQ ID NO: 1. The sequence was analyzed with the DNASIS program (Hitachi Software Engineering Co.) for homology with other sequences from GENBANK and EMBL. No simple homology of this sequence with any sequence from the GENBANK database was found. The greatest maximum matching found was 72.5% over a stretch of 98 base pairs, indicating that PDF is a novel polypeptide.

EXAMPLE 4

Effect of PDF on Prostatic Cancer Cells

Figure 7:
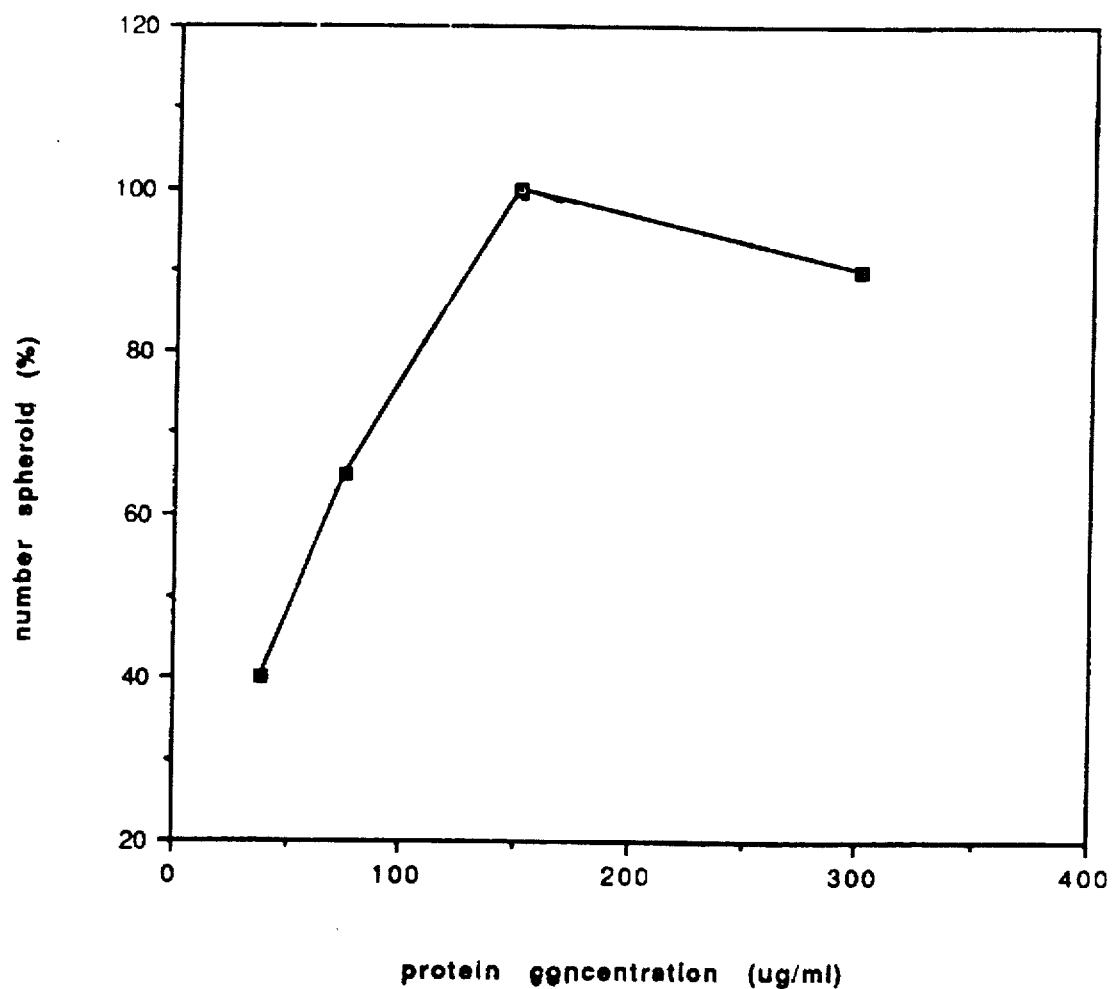
FIG. 7 is a graph demonstrating the effect of PDF on spheroid formation in DU-145 cells.

The human prostatic cell line DU145 was obtained from the American Type Culture Collection and grown in RPMI 1640 medium supplemented with 10% fetal bovine serum (FBS) (BioWhittacker, Walkersville, MC.), 10 IU penicillin/ml 50 mg streptomycin/ml, at 37° C. in a humidified atmosphere containing 5% $CO_2$ To look for the effect of PDF on these cells, cultures containing $1 \times 10^5$ DU-145 cells in serum free-RPMI 1640 medium were treated with various concentrations of PDF (50–300 µg/ml culture). Three days later, the cultures were scored for the formation of spheroids. A correlation between PDF concentration and the number of spheroids formed was found, as depicted by the graph in FIG. 7.

Figure 3:
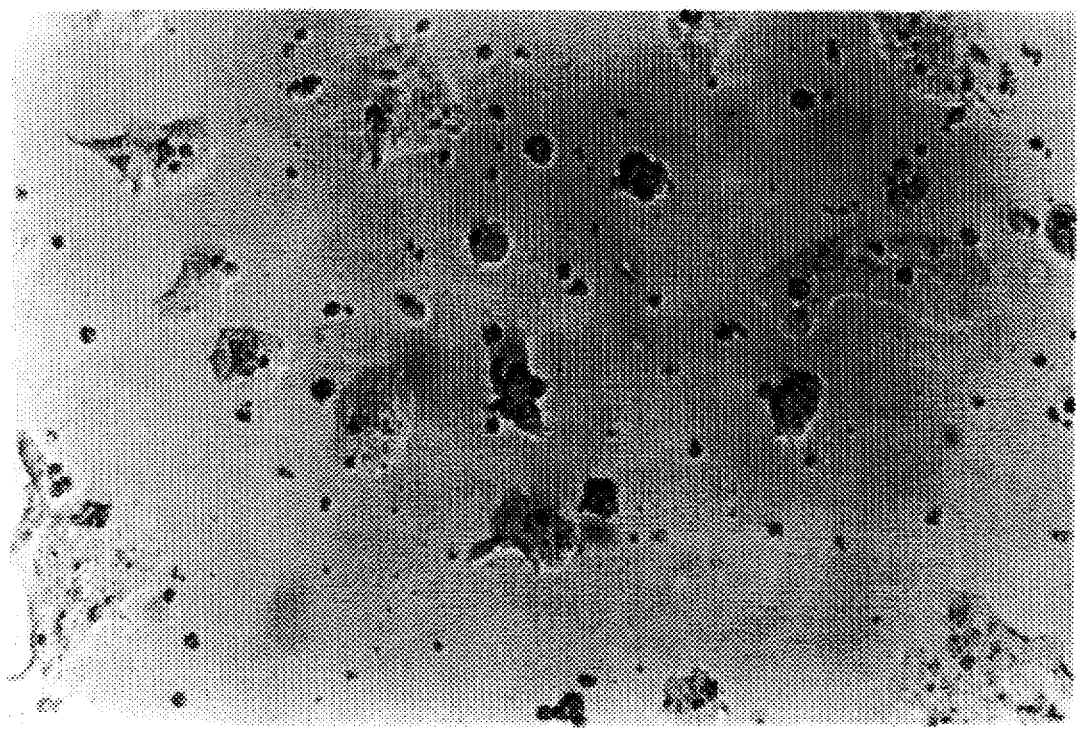
FIG. 3 depicts DU145 prostate cancer cells cultured in the absence of PDF.
Figure 4:
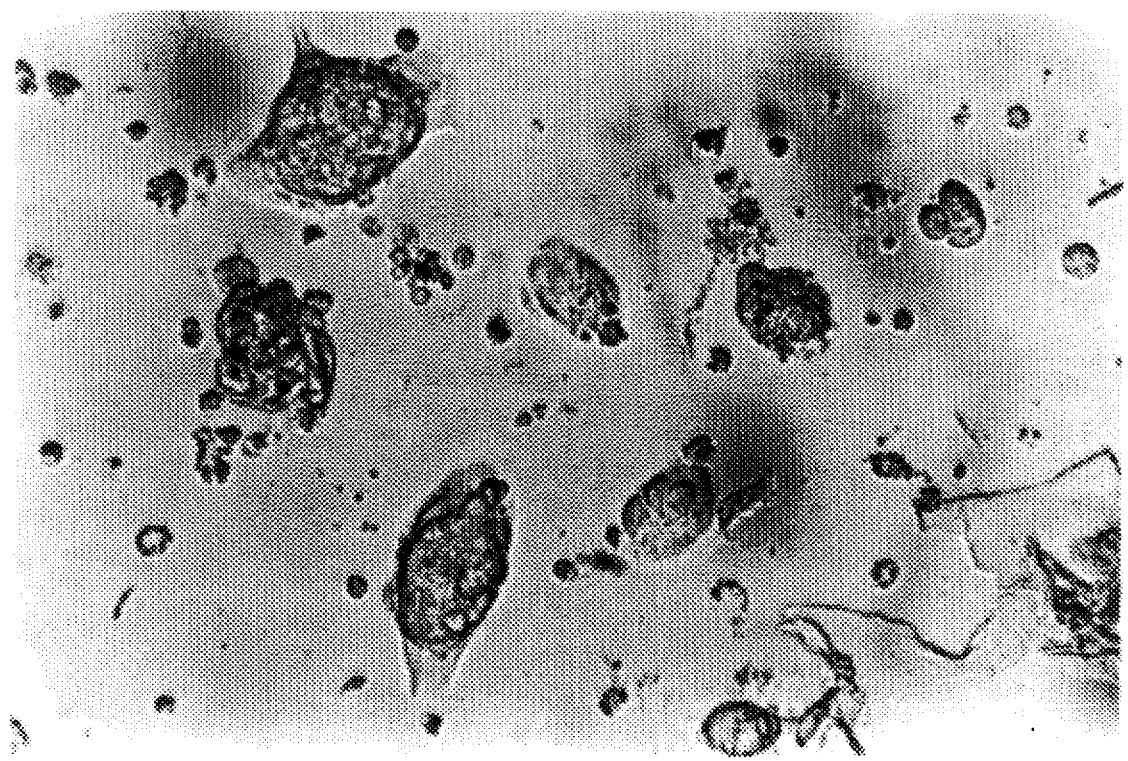
FIG. 4 illustrates the morphological changes, including aggregation and spheroid formation, induced by PDF on DU145 cells.

FIG. 3 depicts DU145 cells cultured in the absence of PDF. FIG. 4 illustrates the morphological changes induced by 150 µg PDF/ml on DU145 prostate cancer cells after 72 hours. The PDF-treated cells aggregated and formed spheroids similar to those produced by breast cancer cells treated with PDF.

EXAMPLE 5

Sequencing and Expression of PDF

The complete nucleotide sequence of the PDF cDNA described in Example 3 is determined by a primer extension strategy as described, for example, by Sambrook et al. From the complete sequence, the start and stop codons, open reading frame and deduced amino acid sequence are determined.

Baculovirus expression vectors containing the cDNA encoding PDF are prepared. The PDF cDNA is cloned into the baculovirus vector AcNPv, and the recombinant baculovirus vector is used to transform cells of the insect cell line Sf21. The baculovirus/insect system is cultured to express recombinant PDF, which is then purified from the culture media or cell extracts. Biological activity of recombinant PDF is confirmed by the in vitro aggregation assay.

EXAMPLE 6

Effect of Recombinant PDF on Tumor Growth

Nude mice bearing the mammary tumor MTW9 are obtained by transplantation as described by Diamond et al. (1976) Cancer Research 36: 77. Recombinant PDF is administered to the tumor-bearing mice by intraperitoneal injection for 21 days at a dosage of 50 µg/kg per day. Reduction in tumor size in response to treatment with PDF is assessed at regular intervals by measuring tumor length, width and height with calipers and calculating tumor volume.

Various publications are cited herein, the contents of which are hereby incorporated by reference in their entireties.

---

We claim:

1. An isolated nucleic acid fragment that specifically hybridizes under high stringency conditions to a nucleic acid having SEQ ID NO:1 or the nucleic acid complementary thereto, wherein said isolated nucleic acid encodes pituitary differentiation factor.

2. An isolated nucleic acid fragment encoding pituitary differentiation factor wherein said isolated nucleic acid comprises the nucleotide sequence of SEQ ID NO: 1.

3. An isolated nucleic acid consisting of a continuous fragment of plasmid pBS-PDF1 wherein said isolated nucleic acid pituitary differentiation factor.

4. The isolated nucleic acid of claim 3 which is 2.2 kilobases in length.

5. An isolated nucleic acid fragment that specifically hybridizes under high stringency conditions to the complement of the nucleic acid of claim 3 wherein said isolated nucleic acid encodes pituitary differentiation factor.

6. A recombinant vector comprising the isolated nucleic acid of claim 1.

7. A recombinant vector comprising the isolated nucleic acid of claim 5.

8. Plasmid pBS-PDF1.

9. A host cell comprising the vector of claim 6.

10. A host cell comprising the vector of claim 7.

11. Isolated and purified pituitary differentiation factor having an amino acid sequence encoded by the nucleic acid of claim 5.

12. Isolated and purified pituitary differentiation factor comprising an amino acid sequence encoded by a nucleic acid having the sequence of SEQ ID NO:1.

13. A method of making pituitary differentiation factor comprising introducing the nucleic acid of claim 1 into a host cell, culturing said host cell under conditions whereby said nucleic acid is expressed, and recovering pituitary differentiation factor.

14. A method of making pituitary differentiation factor comprising introducing the nucleic acid of claim 5 into a host cell, culturing said host cell under conditions whereby said nucleic acid is expressed, and recovering pituitary differentiation factor.

15. A composition consisting essentially of the pituitary differentiation factor of claim 11 and a carrier.

* * * * *

UNITED STATES PATENT AND TRADEMARK OFFICE
CERTIFICATE OF CORRECTION

PATENT NO. : 5,795,740

DATED : August 18, 1998

INVENTOR(S) : Platica et al.

It is certified that error appears in the above-identified patent and that said Letters Patent is hereby corrected as shown below:

Col. 9, line 5, "Endocrinology 1 : 2573" should read --Endocrinology 131 : 2573--.

Col. 15, lines 29-30, "nucleric acid pituitary" should read --nucleic acid encodes pituitary--.

Signed and Sealed this

Sixteenth Day of November, 1999

*Attest:*

*Attesting Officer*

Q. TODD DICKINSON

*Acting Commissioner of Patents and Trademarks*